United States Patent
Serizawa et al.

(10) Patent No.: US 8,420,599 B2
(45) Date of Patent: Apr. 16, 2013

(54) BONE-REINFORCING FOOD MATERIAL

(75) Inventors: Atsushi Serizawa, Saitama (JP); Yoshikazu Morita, Saitama (JP); Daisuke Uetsuji, Saitama (JP); Aiko Ono, Saitama (JP); Hiroaki Matsuyama, Saitama (JP); Satoshi Higurashi, Saitama (JP)

(73) Assignee: MegMilk Snow Brand Co., Ltd., Sapporo (JP)

( * ) Notice: Subject to any disclaimer, the term of this patent is extended or adjusted under 35 U.S.C. 154(b) by 7 days.

(21) Appl. No.: 12/740,709

(22) PCT Filed: Oct. 28, 2008

(86) PCT No.: PCT/JP2008/003064
§ 371 (c)(1),
(2), (4) Date: Jul. 14, 2010

(87) PCT Pub. No.: WO2009/057280
PCT Pub. Date: May 7, 2009

(65) Prior Publication Data
US 2010/0298228 A1 Nov. 25, 2010

(30) Foreign Application Priority Data
Nov. 1, 2007 (JP) ................................ 2007-285377

(51) Int. Cl.
*A61K 38/00* (2006.01)
*A61P 19/08* (2006.01)

(52) U.S. Cl.
USPC ........................................................ 514/16.7

(58) Field of Classification Search ................ None
See application file for complete search history.

(56) References Cited

U.S. PATENT DOCUMENTS

| | | |
|---|---|---|
| 4,667,018 A | 5/1987 | Prieels et al. |
| 4,946,944 A | 8/1990 | Frankinet et al. |
| 4,997,914 A | 3/1991 | Kawakami et al. |
| 5,654,019 A | 8/1997 | Kobayashi et al. |
| 5,932,259 A | 8/1999 | Kato et al. |
| 5,976,597 A | 11/1999 | Takada et al. |
| 2010/0234296 A1 | 9/2010 | Serizawa et al. |
| 2010/0261883 A1 | 10/2010 | Serizawa et al. |
| 2010/0298204 A1 | 11/2010 | Serizawa et al. |

FOREIGN PATENT DOCUMENTS

| | | |
|---|---|---|
| EP | 0348508 | 1/1990 |
| EP | 0704218 | 4/1996 |
| EP | 0786473 | 7/1997 |
| EP | 2208733 | 7/2010 |
| EP | 2208734 | 7/2010 |
| EP | 2208735 | 7/2010 |
| JP | 61-246198 | 11/1986 |
| JP | 63-255300 | 10/1988 |
| JP | 64-86839 | 3/1989 |
| JP | 5-202098 | 8/1993 |
| JP | 0556083 | 8/1993 |
| JP | 5-320066 | 12/1993 |
| JP | 2974604 | 11/1999 |
| JP | 3092874 | 9/2000 |
| JP | 3112637 | 11/2000 |
| JP | 3160862 | 4/2001 |
| JP | 2004-115509 | 4/2004 |
| JP | 2007-246413 | 9/2007 |
| WO | 93/12807 | 7/1993 |
| WO | WO 2004/082397 | * 9/2004 |

OTHER PUBLICATIONS

Protease Finder by Sigma-Aldrich < http://www.sigmaaldrich.com/life-science/metabolomics/enzyme-explorer/learning-center/protease-finder.html > Downloaded Sep. 7, 2012.*
English language Abstract of JP 4-183371, corresponding to JP 3160862, Apr. 25, 2001.
English language Abstract of JP 5-176715, corresponding to JP 3092874, Sep. 25, 2000.
International Search Report that issued with respect to PCT/JP2008/003064, mailed Nov. 25, 2008.
International Preliminary Report on Patentability, including the Written Opinion (in English) for PCT/JP2008/003064, mailed Jun. 10, 2010.
Search report from E.P.O. that issued with respect to patent family member European Patent Application No. 08845996.1, mail date is Sep. 15, 2011.
U.S. Appl. No. 12/740,752 to Atsushi Serizawa et al., which application is the National Stage of PCT/JP2008/003065 filed Oct. 28, 2008.
U.S. Appl. No. 12/740,711 to Atsushi Serizawa et al., which application is the National Stage of PCT/JP2008/003066 filed Oct. 28, 2008.

* cited by examiner

*Primary Examiner* — Suzanne M Noakes
(74) *Attorney, Agent, or Firm* — Greenblum & Bernstein, P.L.C.

(57) ABSTRACT

Disclosed is a bone-reinforcing agent which comprises a milk protein fraction having the following properties (1) to (4): (1) the milk protein fraction is derived from milk; (2) the milk protein fraction is a fraction containing a protein component having a molecular weight of 6,000 to 150,000 Daltons; (3) the milk protein fraction has a basic amino acid content of 12 to 14 wt % in the constitutional amino acid composition, and the ratio of the amount of a basic amino acid(s) to the amount of an acidic amino acid(s) is 0.5 to 0.7; and (4) the milk protein fraction has an activity of accelerating the calcification in an osteoblast.

17 Claims, 1 Drawing Sheet

BONE-REINFORCING FOOD MATERIAL

TECHNICAL FIELD

The present invention relates to a milk protein fraction or a milk protein fraction degradation product that exhibits a bone-reinforcing effect.

Since the milk protein fraction or the milk protein fraction degradation product according to the present invention exhibits a bone-reinforcing effect, the milk protein fraction or the milk protein fraction degradation product is useful as a bone-reinforcing agent that aims at preventing or treating bone diseases or strengthening a bone, and is also useful as an active ingredient of a pharmaceutical, food, drink, or feed that aims at preventing or treating bone diseases or strengthening a bone.

BACKGROUND ART

In recent years, various bone diseases, such as osteoporosis, bone fractures, lumbago or the like have increased along with the progressive increase in the elderly population. In a bone tissue, osteogenesis and bone resorption incessantly occur. In a young person, a balance between osteogenesis and bone resorption is kept, but the balance is disrupted to bone resorption owing to various causes with aging (uncoupling). Continuance of this state for a long period of time makes the bone tissue fragile, resulting in occurrence of various bone diseases, such as osteoporosis, bone fractures, and lumbago. It is considered that prevention of the uncoupling enables prevention of various bone diseases, such as osteoporosis, bone fractures, and lumbago.

Conventionally, in order to prevent the uncoupling to prevent or treat bone diseases, the following methods have been performed: (1) calcium supplementation by diet, (2) light exercise, (3) insolation, (4) medication, and the like. For calcium supplementation by diet, there are used calcium salts, such as calcium carbonate, calcium phosphate or the like, or natural calcium agents such as eggshell, fish bone powder or the like. However, these materials are not necessarily suitable for oral intake. Jogging, walking, or the like may be recommended as light exercise. However, even light exercise is troublesome for a person whose body has weakened, and it is almost impossible for a bedridden old person to do exercise. It is considered that insolation is a good means to supplement activated vitamin $D_3$, but it is not sufficient in itself. 1α-Hydroxyvitamin $D_3$, a calcitonin preparation, or the like is used for administration of a pharmaceutical, and is known to be effective for treating osteoporosis. However, these substances are pharmaceuticals themselves and cannot be used as a food material.

The inventors of the present invention have searched for a bone-reinforcing factor contained in milk in order to obtain a bone-reinforcing substance that can be used as a food material. As a result, the inventors found that a protein and a peptide mixture obtained by removing a salt derived from a milk serum from a water-soluble fraction of a milk serum protein exhibit a bone-reinforcing effect (see Patent Document 1, for example). The inventors found that a fraction obtained by subjecting an aqueous solution of the protein and the peptide mixture to an ethanol treatment, a heat treatment, a salting treatment, and an ultrafiltration membrane treatment exhibits an osteoblast growth promoting effect and a bone-reinforcing effect (see Patent Documents 2 and 3, for example). The inventors further found that a basic protein contained in milk exhibits an osteoblast growth promoting effect, a bone-reinforcing effect, and a bone resorption prevention effect (see Patent Document 4, for example).

Patent Document 1: Japanese Patent No. 3160862
Patent Document 2: Japanese Patent No. 3092874
Patent Document 3: JP-A-H05-320066
Patent Document 4: Japanese Patent No. 3112637

DISCLOSURE OF THE INVENTION

Problems to be Solved by the Invention

An object of the present invention is to provide a milk protein fraction or a milk protein fraction degradation product that exhibits a bone-reinforcing effect and can be used as a food material, a bone-reinforcing agent containing the milk protein fraction or the milk protein fraction degradation product that exhibits a bone-reinforcing effect, and a pharmaceutical, food, drink, or feed containing the milk protein fraction or the milk protein fraction degradation product that exhibits a bone-reinforcing effect.

Means for Solving the Problems

The inventors searched for a novel bone-reinforcing material, and found that a fraction exhibiting a high bone-reinforcing effect as compared with a known food material could be obtained. Based on those findings, the inventors thus obtained a bone-reinforcing agent containing the milk protein fraction or the milk protein fraction degradation product that exhibits a bone-reinforcing effect, and a pharmaceutical, food, drink, or feed containing the milk protein fraction or the milk protein fraction degradation product that exhibits a bone-reinforcing effect.

Specifically, the present invention is constituted as follows:
(A) A milk protein fraction characterized in that (1) the milk protein fraction is derived from milk, (2) the milk protein fraction contains proteins having a molecular weight of 6000 to 150,000 daltons determined by sodium dodecyl sulfate-polyacrylamide gel electrophoresis (SDS-PAGE), (3) the milk protein fraction contains 12 to 14 wt % of basic amino acids in the constituent amino acid composition, and has a basic amino acid/acidic amino acid ratio of 0.5 to 0.7, and (4) the milk protein fraction has a promoting effect on calcification in an osteoblast.
(B) A milk protein fraction degradation product obtained by degrading the above milk protein fraction with a protease.
(C) A bone-reinforcing agent comprising the milk protein fraction or the milk protein fraction degradation product according to (A) or (B), respectively.
(D) A bone-reinforcing pharmaceutical comprising the milk protein fraction according to (A) or the milk protein fraction degradation product according to (A) or (B), respectively.
(E) A bone-reinforcing food or drink comprising the milk protein fraction or the milk protein fraction degradation product according to (A) or (B), respectively.
(F) A bone-reinforcing feed comprising the milk protein fraction or the milk protein fraction degradation product according to (A) or (B), respectively.

Effects of the Invention

The bone-reinforcing agent containing the milk protein fraction or the milk protein fraction degradation product that exhibits a bone-reinforcing effect as an active ingredient, and the bone-reinforcing pharmaceutical, food, drink, or feed containing the milk protein fraction or the milk protein fraction degradation product that exhibits a bone-reinforcing effect according to the present invention promote calcification in an osteoblast in a body when taken orally.

Therefore, the bone-reinforcing agent containing the milk protein fraction or the milk protein fraction degradation product that exhibits a bone-reinforcing effect as an active ingredient, and the bone-reinforcing pharmaceutical, food, drink, or feed containing the milk protein fraction or the milk protein fraction degradation product that exhibits a bone-reinforcing effect according to the present invention exhibit a bone-reinforcing effect by promoting calcification in an osteoblast in the body of a human or an animal, and are effective for suppressing a decrease in bone mass due to osteoporosis or the like.

BEST MODE FOR CARRYING OUT THE INVENTION

Figure 1:
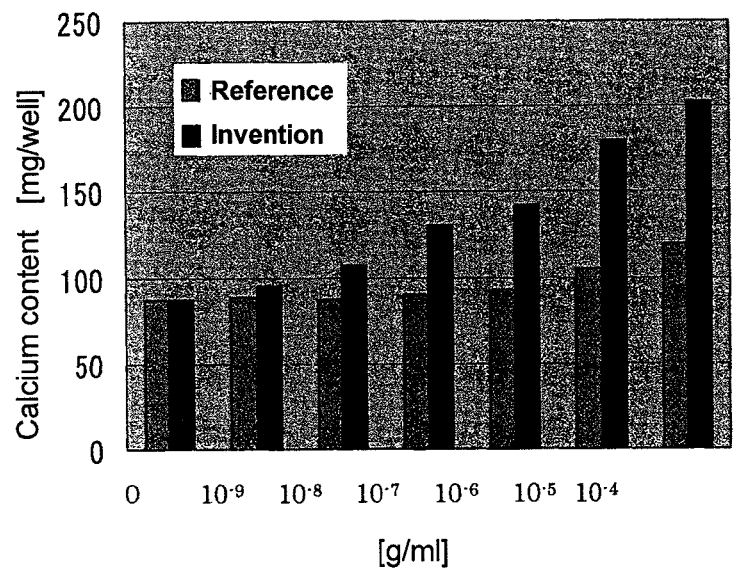
FIG. 1 is a view illustrative of the calcification promoting effect of a milk protein fraction (Test example 1).

The present invention relates to a bone-reinforcing agent including a milk protein fraction or a milk protein fraction degradation product that exhibits a bone-reinforcing effect as an active ingredient, as well as a bone-reinforcing pharmaceutical, food or drink, and feed including a milk protein fraction or a milk protein fraction degradation product that exhibits a bone-reinforcing effect.

The milk protein fraction according to the present invention that exhibits a bone-reinforcing effect may be obtained by bringing a milk raw material, such as skim milk, milk serum or the like into contact with a cation-exchange resin, washing the cation-exchange resin with deionized water, and eluting the milk protein adsorbed on the cation-exchange resin using a 0.2M sodium chloride eluant. Note that salt such as a potassium salt, an ammonium salt, a phosphate, an acetate, a carbonate, or the like may be used in addition to sodium chloride. The milk protein fraction according to the present invention may be obtained by appropriately adjusting the ionic strength of the washing agent to 0.05 or less and the ionic strength of the elution solution to 0.15 to 0.25. Furthermore, the milk protein fraction according to the present invention may be obtained by collecting the eluted fraction, desalting and concentrating the fraction using a reverse osmosis (RO) membrane, electrodialysis (ED), or the like, and optionally drying the resulting product. Examples of the reverse osmosis (RO) membrane include Desal-3 (manufactured by Desalination), HR-95 (manufactured by Dow Danmark), NTR-729HF (manufactured by Nitto Denko Corporation), and the like. Examples of an electrodialysis (ED) system include electrodialysis systems manufactured by Yuasa-Ionics Inc. and Nippon Rensui Co., Ltd.

As a method of obtaining a protein fraction derived from milk, a method of obtaining a protein fraction by bringing milk or a raw material derived from milk into contact with a cation exchanger, and eluting the basic protein fraction that is adsorbed on the cation exchanger using an eluant that has a pH of more than 5 and an ionic strength of more than 0.5 (JP-A-H05-202098), a method of obtaining a protein fraction using an alginic acid gel (JP-A-S61-246198), a method of obtaining a protein fraction from a milk serum using porous inorganic particles (JP-A-H01-86839), a method of obtaining a protein fraction from milk using a sulfated ester compound (JP-A-S63-255300), and the like have been known. Protein fractions obtained by those methods may be used as the protein fraction that is derived from milk and exhibits a bone-reinforcing effect according to the present invention.

The milk protein fraction thus collected may be normally powdered by freeze-drying or the like before use.

The milk protein fraction that exhibits a bone-reinforcing effect used in the present invention preferably contains 12 to 14 wt % of basic amino acids in the constituent amino acid composition, and has a basic amino acid/acidic amino acid ratio of 0.5 to 0.7. The effect of the present invention may not be achieved if the content of basic amino acids or the basic amino acid/acidic amino acid ratio is outside the above range. The milk protein fraction according to the present invention is a mixture of various proteins having a molecular weight of 6000 to 150,000 daltons, and the isoelectric point thereof is widely distributed in a range of 6 to 11.

The milk protein fraction degradation product has the same amino acid composition as that of the milk protein fraction. For example, a milk protein fraction degradation product having an average molecular weight of 4000 or less may be obtained by treating a milk protein fraction obtained by the above method with a protease such as pepsin, trypsin, chymotrypsin or the like, and optionally treating the resulting product with a protease such as pancreatin or the like. The milk protein fraction degradation product is normally powdered by freeze-drying or the like before use.

As milk or a raw material derived from milk which can be used as source of the milk protein fraction according to the present invention that exhibits a bone-reinforcing effect, cow milk, human milk, goat milk, ewe milk or the like may be given. Such milks may be used as is, or recombined milk, skim milk, whey, or the like derived from such milks may be used.

The milk protein fraction or the milk protein fraction degradation product that exhibits a bone-reinforcing effect and is an active ingredient may be used as is when administering the bone-reinforcing agent according to the present invention. Note that it is also possible to use after being formulated into a powdered pharmaceutical, granules, a tablet, a capsule, a drinkable preparation, or the like in accordance with a conventional method. Moreover, the milk protein fraction or the milk protein fraction degradation product, as is or after formulating a preparation thereof, may be added to a nutrient preparation, food and drink, or the like to achieve a bone-reinforcing effect. Since the milk protein fraction or the milk protein fraction degradation product according to the present invention is relatively stable against heat, the milk protein fraction or the milk protein fraction degradation product can be heat-sterilized under conventional conditions.

In the present invention, in order to achieve a bone-reinforcing effect the dosage or the like may be appropriately determined taking account of weight, sex, age, and the like. The milk protein fraction or the milk protein fraction degradation product may be adjusted the formulating amount thereof so that a normal adult takes the milk protein fraction or the milk protein fraction degradation of the present invention in an amount of 1 to 50 mg/day. That is, the milk protein fraction or the milk protein fraction degradation product according to the present invention is effective at a low dosage. In the present invention, the ingredient having a bone-reinforcing effect exerts the bone-reinforcing effect when orally administered a bone-reinforcing agent or a pharmaceutical, food and drink, or feed formulated the bone-reinforcing agent The present invention is further described below by way of reference examples, examples, and test examples. Note that the following examples merely illustrate several aspects of the present invention, and should not be construed as limiting the present invention.

Reference Example 1

A milk protein fraction exhibiting a bone-reinforcing effect which was commercially available was prepared in accordance with the following method (see Japanese Patent No. 3112637).

A column (diameter: 10 cm) loaded with 0.5 litters of sulfonated Chitopearl (cation-exchange resin; manufactured by Fuji Spinning Co., Ltd.) was sufficiently washed with deionized water. After passing 50 l of unsterilized skim milk through the column at a flow rate of 100 ml/min, the column was sufficiently washed with deionized water. 2.5 l of a 0.05M phosphate buffer (pH 7.0) containing 0.95M sodium chloride was then passed through the column to elute proteins adsorbed on the resin. The eluate was desalted and concentrated by means of a reverse osmosis (RO) membrane treatment, and then freeze-dried to obtain a powdery milk protein fraction. The above procedure was repeated twice to obtain $10^4$ g of a protein fraction. The protein fraction had an isoelectric point of 7.0 to 8.5. The content of basic amino acids in the protein fraction was 17.8%.

Example 1

A column (diameter: 10 cm) loaded with 0.5 l of sulfonated Chitopearl (cation-exchange resin; manufactured by Fuji Spinning Co., Ltd.) was sufficiently washed with deionized water. After passing 50 l of unsterilized skim milk through the column at a flow rate of 100 ml/min, the column was sufficiently washed with deionized water. 2.5 l of a 0.05M phosphate buffer (pH 7.0) containing 0.15M sodium chloride was then passed through the column to elute proteins adsorbed on the resin. The eluate was desalted and concentrated by means of a reverse osmosis (RO) membrane treatment, and then freeze-dried to obtain a powdery milk protein fraction. The above procedure was repeated ten times to obtain 24.2 g of a protein fraction. The protein fraction had a molecular weight of 6000 to 150,000 daltons and an isoelectric point of 6.0 to 11.0. The content of basic amino acids in the constituent amino acid contained in the protein fraction was 12 to 14%. The protein fraction had a basic amino acid/acidic amino acid ratio of 0.5 to 0.7.

Example 2

A column (diameter: 10 cm) loaded with 0.5 l of sulfonated Chitopearl (cation-exchange resin; manufactured by Fuji Spinning Co., Ltd.) was sufficiently washed with deionized water. After passing 50 l of unsterilized skim milk through the column at a flow rate of 100 ml/min, the column was sufficiently washed with a 0.05M phosphate buffer (pH 7.0) containing 0.05M sodium chloride. 2.5 l of a 0.05M phosphate buffer (pH 7.0) containing 0.25M sodium chloride was then passed through the column to elute proteins adsorbed on the resin. The eluate was desalted and concentrated by means of a reverse osmosis (RO) membrane treatment, and then freeze-dried to obtain a powdery milk protein fraction. The above procedure was repeated five times to obtain 12.8 g of a protein fraction. The protein fraction had a molecular weight of 6000 to 150,000 daltons and an isoelectric point of 6.0 to 11.0. The content of basic amino acids in the constituent amino acid contained in the protein fraction was 12 to 14%. The protein fraction had a basic amino acid/acidic amino acid ratio of 0.5 to 0.7.

Example 3

24.2 g of the milk protein fraction obtained in Example 1 was dissolved in 10 l of distilled water. After adding pepsin (manufactured by Kanto Kagaku Co., Ltd.) so as to be the concentration of 2%, the milk protein fraction was hydrolyzed at 37° C. for one hour with stirring. After the mixture was neutralized to pH 6.8 with a sodium hydroxide solution, 1% pancreatin (manufactured by Sigma) was added thereto. The mixture was then reacted at 37° C. for two hours. After completion of the reaction, the protease was inactivated by heating the mixture at 80° C. for 10 minutes to obtain 23.1 g of a milk protein fraction degradation product.

Example 4

12.8 g of the milk protein fraction obtained in Example 2 was dissolved in 8 l of distilled water. After adding trypsin (manufactured by Kanto Kagaku Co., Ltd.) so as to be the concentration of 2%, the milk protein fraction was hydrolyzed at 37° C. for one hour with stirring. After the mixture was neutralized to pH 6.6 with a sodium hydroxide solution, 1% pancreatin (manufactured by Sigma) was added thereto. The mixture was then reacted at 37° C. for two hours. After completion of the reaction, the protease was inactivated by heating the mixture at 80° C. for 10 minutes to obtain 11.7 g of a milk protein fraction degradation product.

Test Example 1

The protein fractions obtained in Reference example 1 and Example 1 were tested in accordance with the method proposed by Danjo et al. (Danjo. A. et al., Biochem. Biophys. Res. Commun., vol. 360, pp. 199-204, 2007). Specifically, mouse calvaria derived osteoblast-like cells MC3T3-E1 were suspended in an αMEM+10% FBS medium so that the cell density was $5 \times 10^3$ cells/cm$^2$, and seeded in a 24-well culture plate. After allowing the cells to stand for 12 hours, the medium was replaced with a calcification medium (αMEM+ 10% FBS 50 μg/ml+5 mM β-glycerophospho acid), and the milk protein obtained in Reference example 1 or the milk protein obtained in Example 1 was added to a concentration of $10^{-10}$ to $10^{-5}$ M. The cells were cultured for 28 days while exchanging the medium every three days.

On the 14th, 21st, or 28th day, the cells were fixed at room temperature for 10 minutes using a 0.1M phosphate buffer (pH 7.4) containing 4% paraformaldehyde. After washing with 0.01M PBS, the cells were reacted with a 2% alizarin red S aqueous solution at room temperature for 15 minutes to be subjected to calcium staining. In order to stain phosphoric acid, which is one of inorganic component of bone, the fixed cells were washed with distilled water, and reacted with a 5% silver nitrate aqueous solution at room temperature for one hour to be subjected to von Kossa staining. A calcium C kit (manufactured by Wako Pure Chemical Industries, Ltd.) was used to determine the amount of calcium ions in the calcified nodule.

FIG. 1 shows the calcium content measurement results obtained on the 28th day. A group cultured in only a medium to which the sample was not added was used as a control.

The milk protein of the present invention obtained in Example 1 was admitted to promote calcification in the osteoblast in proportion to the dosage. The milk protein obtained in Reference example 1 was also admitted a similar effect, but the osteoblast calcification promotion effect was determined to be weaker in comparison with the present invention.

Test Example 2

The bone-reinforcing effect of the protein fractions obtained in Reference example 1 and Example 1 was investigated by animal experiments. Wistar rats (female, 4 weeks old) were used for the animal experiments. After preliminary feeding for one week, the ovary was removed from each rat. A calcium-deficient food was then fed to the rats for five weeks. The rats from which the ovary was removed and to which the calcium-deficient food were fed had osteoporosis obviously. The rats having osteoporosis were divided into 5 experiment group (six rats per each group) of a control group (Group A) that was not administered a milk protein fraction, a group (Group B) that was administered 0.5 wt % of the milk protein fraction obtained in Reference example 1, a group (Group C) that was administered 0.1 wt % of the milk protein fraction obtained in Example 1, a group (Group D) that was administered 0.5 wt % of the milk protein fraction obtained in Example 1, and a group (Group E) that was administered 1.0 wt % of the milk protein fraction obtained in Example 1. A test feed shown in Table 1 was fed to each group for four months. The nitrogen content in each test feed was adjusted to 17.06% using casein. Each test feed was blended with 300 mg of calcium, 230 mg of phosphorus and 50 mg of magnesium per 100 g of the test feed.

TABLE 1

| | Group | | | | |
|---|---|---|---|---|---|
| | A | B | C | D | E |
| Casein | 20.0 | 19.5 | 19.9 | 19.5 | 19.0 |
| Cornstarch | 15.0 | 15.0 | 15.0 | 15.0 | 15.0 |
| Cellulose | 5.0 | 5.0 | 5.0 | 5.0 | 5.0 |
| Corn oil | 5.0 | 5.0 | 5.0 | 5.0 | 5.0 |
| Vitamin mix | 1.0 | 1.0 | 1.0 | 1.0 | 1.0 |
| Mineral mix | 2.65 | 2.65 | 2.65 | 2.65 | 2.65 |
| Sucrose | 51.05 | 51.05 | 51.05 | 51.05 | 51.05 |
| DL-Methionine | 0.3 | 0.3 | 0.3 | 0.3 | 0.3 |
| Milk protein fraction obtained in Reference example 1 | — | 0.5 | — | — | — |
| Milk protein fraction obtained in Example 1 | — | — | 0.1 | 0.5 | 0.1 |

(wt %)

Figure 2:
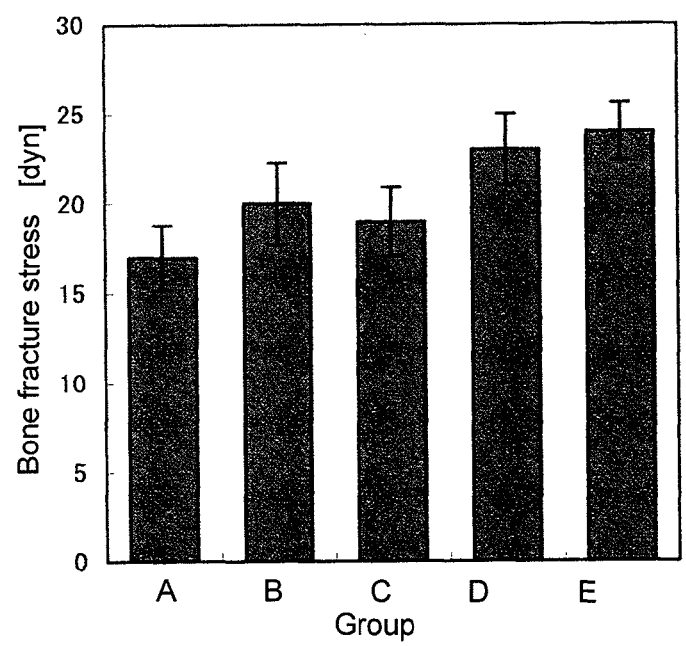
FIG. 2 is a view showing a thighbone strength enhancement effect when administering a milk protein fraction obtained in Example 1 of the present invention to rats having osteoporosis (Test example 2).

After four months, the thighbones of both legs were removed from the rats of each test group, and the bone strength was measured using a bone fracture measuring instrument ("Rheometer Max RX-1600" manufactured by Aitecno Inc.). The results are shown in FIG. 2. As shown in FIG. 2, the thighbone fracture stresses of the group (Group B) that was administered the milk protein fraction obtained in Reference example 1 and the groups (Groups C, D, and E) that were administered the milk protein fraction obtained in Example 1 were found to be higher than that of the control group (Group A. no addition of milk protein fraction). The thighbone fracture stress increased as the increase of the concentration of the milk protein fraction obtained in Example 1. Though the milk protein fraction obtained in Reference example 1 showed an effect of increasing the thighbone fracture stress, the effect was found to be weaker than that of the milk protein fraction obtained in Example 1.

Similar effects were observed when using the milk protein fraction degradation products obtained in Examples 3 and 4 (but not shown in FIG. 2).

Example 5

100 mg of the milk protein fraction obtained in Example 1 was added with 93.4 g of crystalline glucose hydrate, 5 g of calcium carbonate, 1 g of a sugar ester, and 0.5 g of flavor, and the mixture was mixed. The resultant was then formed into a tablet to obtain a bone-reinforcing agent according to the present invention.

Example 6

The components were mixed in accordance with the composition shown in Table 2 to obtain a dough. The dough was formed and baked to produce a cookie for preventing or alleviating various bone diseases, such as osteoporosis.

TABLE 2

| Flour | 50.0 (wt %) |
|---|---|
| Sugar | 20.0 |
| Salt | 0.5 |
| Margarine | 12.5 |
| Egg | 12.1 |
| Water | 4.0 |
| Sodium hydrogen carbonate | 0.1 |
| Ammonium bicarbonate | 0.2 |
| Calcium carbonate | 0.5 |
| Milk protein fraction powder (Example 1) | 0.1 |

Example 7

A bone-reinforcing fruit juice drink having a composition shown in Table 3 was produced.

TABLE 3

| Mixed isomerized sugar | 15.0 (wt %) |
|---|---|
| Fruit juice | 10.0 |
| Citric acid | 0.5 |
| Milk protein fraction powder (Example 1) | 0.5 |
| Flavor | 0.1 |
| Calcium | 0.1 |
| Water | 73.8 |

Example 8

The ingredients were mixed in accordance with the formulation shown in Table 4 to produce a bone-reinforcing dog food.

TABLE 4

| Milk protein fraction powder (Example 1) | 2.5 (wt %) |
|---|---|
| Skim milk powder | 13.5 |
| Soybean cake | 12.0 |
| Soybean oil | 4.0 |
| Corn oil | 2.0 |
| Palm oil | 27.0 |
| Corn starch | 14.0 |
| Wheat powder | 9.0 |
| Wheat bran | 2.0 |
| Vitamin mix | 9.0 |
| Mineral mix | 2.0 |
| Cellulose | 3.0 |

Example 9

Each ingredient was mixed in accordance with the formulation shown in Table 5, and formed under pressure to produce a bone-reinforcing tablet containing the milk protein fraction degradation product obtained in Example 3.

TABLE 5

| | |
|---|---|
| Crystalline glucose hydrate | 59.4 (wt %) |
| Milk protein fraction degradation product (Example 3) | 16.0 |
| Corn starch | 12.0 |
| Cellulose | 4.0 |
| Corn oil | 4.0 |
| Vitamin mix (including choline) | 1.0 |
| Mineral mix | 3.6 |

Example 10

Each ingredient was mixed in accordance with the formulation shown in Table 6, and emulsified at 85° C. to produce a bone-reinforcing processed cheese containing the milk protein fraction degradation product obtained in Example 4.

TABLE 6

| | |
|---|---|
| Gouda cheese | 43.0 (wt %) |
| Cheddar cheese | 43.0 |
| Sodium citrate | 2.0 |
| Milk protein fraction degradation product (Example 4) | 0.5 |
| Calcium derived from milk | 1.0 |
| Water | 10.5 |

INDUSTRIAL APPLICABILITY

Since the milk protein fraction according to the present invention exhibits a bone-reinforcing effect, the milk protein fraction is useful for preventing or treating bone diseases as a bone-reinforcing agent that aims at strengthening a bone and the like. Moreover, since the present invention product is safe, it is possible to use as a bone disease prevention/treatment pharmaceutical, food, drink, or feed.

The invention claimed is:

1. A milk protein fraction degradation product obtained by degrading, with trypsin, chymotrypsin, or pepsin, a milk protein fraction having following characteristics (1) to (4): (1) the milk protein fraction is derived from milk, (2) the milk protein fraction comprises proteins and each protein in the milk fraction has a molecular weight of 6000 to 150,000 daltons determined by sodium dodecyl sulfate-polyacrylamide gel electrophoresis (SDS-PAGE), (3) when considered together, the proteins in the milk protein fraction are 12 to 14 percent of basic amino acids by weight of the constituent amino acid composition, and have a basic amino acid/acidic amino acid ratio of 0.5 to 0.7, and (4) the milk protein fraction has a promoting effect on calcification in an osteoblast.

2. A bone-reinforcing agent comprising the milk protein fraction degradation product according to claim 1.

3. A bone-reinforcing pharmaceutical comprising the milk protein fraction degradation product according to claim 1.

4. A bone-reinforcing food or drink comprising the milk protein fraction degradation product according to claim 1.

5. A bone-reinforcing feed comprising the milk protein fraction degradation product according to claim 1.

6. A method of reinforcing bone in a subject comprising orally administering to a subject a composition having the following characteristics (1) to (4):
   (1) comprises components obtained from milk,
   (2) comprises proteins, each of which has a molecular weight of 6000 to 150,000 daltons determined by sodium dodecyl sulfate-polyacrylamide gel electrophoresis (SDS-PAGE),
   (3) when considered together, the proteins in the composition are 12 to 14 percent of basic amino acids by weight of the constituent amino acid composition, and have a basic amino acid/acidic amino acid ratio of 0.5 to 0.7, and
   (4) has a promoting effect on calcification in an osteoblast in vitro;
wherein the administration results in a reinforcing effect on bone in the subject.

7. A method of promoting calcification in osteoblasts comprising orally administering to a subject a composition having the following characteristics (1) to (4):
   (1) comprises components obtained from milk,
   (2) comprises proteins, each of which has a molecular weight of 6000 to 150,000 daltons determined by sodium dodecyl sulfate-polyacrylamide gel electrophoresis (SDS-PAGE),
   (3) when considered together, the proteins in the composition are 12 to 14 percent of basic amino acids by weight of the constituent amino acid composition, and have a basic amino acid/acidic amino acid ratio of 0.5 to 0.7, and
   (4) has a promoting effect on calcification in an osteoblast in vitro;
wherein the administration has a promoting effect on calcification in osteoblasts in the subject.

8. The method according to claim 6, wherein the composition is a milk protein fraction degradation product comprising a milk protein fraction having characteristics (1) to (4), degraded with a protease.

9. The method according to claim 6, wherein the composition is a dry composition.

10. The method according to claim 9, wherein the composition is a baked good.

11. The method according to claim 6, wherein the composition is a liquid composition.

12. The method according to claim 11, wherein the composition is a fruit juice.

13. The method according to claim 6, comprising administering the composition in an amount of 1-50 mg/day.

14. The method according to claim 6, comprising co-administering a calcium supplement with the composition.

15. The method according to claim 6, wherein the subject is a person in recognized need of bone reinforcement.

16. The method according to claim 15, wherein the subject is a person diagnosed with osteoporosis.

17. The method according to claim 15, wherein the subject is a person at recognized risk of osteoporosis.

* * * * *